(12) United States Patent
De Wild et al.

(10) Patent No.: US 11,399,809 B2
(45) Date of Patent: Aug. 2, 2022

(54) PATIENT MONITORING

(71) Applicant: KONINKLIJKE PHILIPS N.V., Eindhoven (NL)

(72) Inventors: Nico Maris Adriaan De Wild, Eindhoven (NL); Igor Wilhelmus Franciscus Paulussen, Nuenen (NL); Rick Bezemer, Eindhoven (NL); Sabina Manzari, Eindhoven (NL); Denny Mathew, Eindhoven (NL); Franciscus Hendrikus Van Heesch, Valkenswaard (NL); Christianus Martinus Van Heesch, Eindhoven (NL); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/767,626

(22) PCT Filed: Nov. 30, 2018

(86) PCT No.: PCT/EP2018/083072
§ 371 (c)(1),
(2) Date: May 28, 2020

(87) PCT Pub. No.: WO2019/110430
PCT Pub. Date: Jun. 13, 2019

(65) Prior Publication Data
US 2020/0367861 A1 Nov. 26, 2020

(30) Foreign Application Priority Data
Dec. 7, 2017 (EP) .................................... 17205929

(51) Int. Cl.
*A61B 8/00* (2006.01)
*A61B 8/06* (2006.01)
(Continued)

(52) U.S. Cl.
CPC .................. *A61B 8/54* (2013.01); *A61B 8/06* (2013.01); *A61B 8/12* (2013.01); *A61B 8/4209* (2013.01);
(Continued)

(58) Field of Classification Search
CPC .... A61B 8/06; A61B 8/12; A61B 8/42; A61B 8/4209; A61B 8/4227; A61B 8/4236;
(Continued)

(56) References Cited

U.S. PATENT DOCUMENTS 7,238,158 B2   7/2007  Abend
7,425,199 B2   9/2008  Hoctor et al.
(Continued)

FOREIGN PATENT DOCUMENTS

WO   2016207889 A1   12/2016
WO   2017093150 A1   6/2017

OTHER PUBLICATIONS

International Search Report and Written Opinion, International Application No. PCT/EP2018/083072, dated Jan. 4, 2019.
(Continued)

*Primary Examiner* — Yi-Shan Yang
*Assistant Examiner* — Alexei Bykhovski

(57) ABSTRACT

Disclosed is a patient monitor control unit (10) comprising a processor arrangement (11, 13) adapted to receive a series of ultrasound measurements received from a sensor (30) comprising at least one configurable ultrasound transducer; process said series of ultrasound measurements to obtain haemodynamic data of a patient coupled to the sensor; control a patient monitor (20) to display the obtained hae-
(Continued)

modynamic data; evaluate the obtained haemodynamic data to detect a variance in said data; and generate a reconfiguration signal for the at least one configurable ultrasound transducer, wherein the timing of said generation is a function of said evaluation. Also disclosed are a patient monitoring system, a method of operating a patient monitor control unit and a computer program product for implementing such a method.

17 Claims, 5 Drawing Sheets

(51) Int. Cl.
*A61B 8/08* (2006.01)
*A61B 8/12* (2006.01)

(52) U.S. Cl.
CPC .......... *A61B 8/4411* (2013.01); *A61B 8/4483* (2013.01); *A61B 8/461* (2013.01); *A61B 8/488* (2013.01); *A61B 8/5223* (2013.01); *A61B 8/56* (2013.01); *A61B 8/58* (2013.01); *A61B 8/4227* (2013.01); *A61B 8/4236* (2013.01)

(58) Field of Classification Search
CPC ... A61B 8/4411; A61B 8/4444; A61B 8/4483; A61B 8/461; A61B 8/488; A61B 8/5223; A61B 8/5269; A61B 8/54; A61B 8/56; A61B 8/58; A61B 8/585
See application file for complete search history.

(56) References Cited

U.S. PATENT DOCUMENTS

| | | |
|---|---|---|
| 2005/0154299 A1 | 7/2005 | Hoctor et al. |
| 2006/0079778 A1* | 4/2006 | Mo ........................ A61B 8/585 600/447 |
| 2010/0312115 A1 | 12/2010 | Dentinger |
| 2011/0201900 A1 | 8/2011 | Zhang et al. |
| 2013/0165785 A1* | 6/2013 | Lause ...................... A61B 8/54 600/443 |
| 2013/0190625 A1 | 7/2013 | Shibamoto et al. |
| 2017/0007853 A1* | 1/2017 | Alford ................. A61B 5/4848 |

OTHER PUBLICATIONS

Shomaji, S. et al., "A Wearable Carotid Ultrasound Assembly for Early Detection of Cardiovascular Diseases", 2016, IEEE Healthcare Innovation Point-of-Care Technologies Conference.
Anonymous, "Patient Monitor", https://www.indiamart.com/olampus-hospital-equipments/icu-equipments.html, Accessed May 26, 2020.

* cited by examiner

PATIENT MONITORING

This application is the U.S. National Phase application under 35 U.S.C. § 371 of International Application No. PCT/EP2018/083072, filed on 30 Nov. 2018, which claims the benefit of European Application Serial No. 17205929.7, filed 7 Dec. 2017. These applications are hereby incorporated by reference herein.

FIELD OF THE INVENTION

The present invention relates to a patient monitor control unit comprising a processor arrangement adapted to control a patient monitor to display haemodynamic data.

The present invention further relates to a patient monitoring system comprising such a patient monitor control unit.

The present invention further relates to computer-implemented method of controlling a patient monitor.

The present invention further relates to a computer program product for implementing such a method.

BACKGROUND OF THE INVENTION

The continuously shrinking form factor of ultrasound devices means that such devices can now be deployed as sensors (also as a wearable sensor), e.g. patches, such as for the sake of (semi-)continuous patient monitoring a clinical setting such as hospital or another medical facility. As is well-known per se, ultrasound devices may be used to collect haemodynamic data through the use of Doppler ultrasound, such as blood flow including peak flow, velocity and vascular diameter from which patient parameters such as arterial perfusion, circulatory volume status, fluid responsiveness, haemodynamic stability and so on may be derived. It for example may be useful to monitor such haemodynamic parameters in haemodynamically unstable patients, e.g. patients recovering from surgery.

Typically, such monitoring results are displayed on a patient monitor, i.e. a display device displaying one or more of such parameters on its display screen, where the parameters may be displayed as traces that progress in time across a dedicated display area such that a caregiver can evaluate the haemodynamic stability of the patient by evaluating the displayed traces. In addition, the patient monitor typically comprises a control unit that evaluates the haemodynamic data in order to generate an alarm upon detecting an anomaly in the haemodynamic data, such that a caregiver can be alerted and provide any medical attention the patient may need.

This is for instance known from US 2010/0312115 A1, which discloses a method for continuous non-invasive hemodynamic state monitoring in a subject by acquiring continuous ultrasound data via an ultrasound transducer attached to the subject. Continuous arterial waveforms are estimated based upon the acquired ultrasound data and hemodynamic parameters are derived for each cardiac cycle from the arterial waveforms. A current hemodynamic state of the subject is defined by setting limits on one or more hemodynamic parameters based upon the variation of these parameters over an initial period of time, which are used to continuously monitor a hemodynamic state of the subject by comparing a current state for one or more hemodynamic parameters of the subject to previously determined limits for the one or more hemodynamic parameters, and either outputting a trigger signal or alarm to a hemodynamic state monitor in an event that a change is detected in the current state of the one or more hemodynamic parameters or converting the arterial parameters into a continuous estimate of the arterial blood pressure in an event that a change is not detected.

When deploying an ultrasound device onto the patient for such monitoring, the ultrasound device is typically configurable in order to find a patient's artery (or organ of interest) for monitoring and/or optimizing the signal to noise ratio of the ultrasound echo signals acquired with the ultrasound device. For example, the ultrasound device may comprise a plurality of ultrasound transducers that may be individually addressed in a configurable manner in order to electronically steer, i.e. vary the angle of, the ultrasound beam produced by the ultrasound device in order to locate the patient's artery in the field of view of the ultrasound device. This may involve manual positioning of the ultrasound device onto the patient followed by electronic configuration of the ultrasound device to obtain the optimal configuration of the ultrasound device in terms of the aforementioned signal to noise ratio of its acquired echo signals.

A problem that is associated with such wearable ultrasound devices is that patient movement may cause the alignment of the ultrasound device relative to the patient's artery (or organ of interest) to be monitored to be disturbed, causing a deterioration in the signal quality produced by the ultrasound device. This will show as a sudden change in the haemodynamic data (including the haemodynamic parameters derived therefrom) on the patient monitor and can trigger false alarms as the cause of the change in the haemodynamic data is unrelated to a medical emergency. This is of course rather undesirable from the perspective of the caregiver, as such false alarms can waste precious time of the caregiver by the caregiver needlessly attending to the patient.

Hence, there exists a need for smart control of the patient monitor such that the generation of such false alarms is at least reduced.

SUMMARY OF THE INVENTION

The present invention seeks to provide a patient monitor control unit comprising a processor arrangement adapted to control a patient monitor to display haemodynamic data that can cause the patient monitor to display accurate haemodynamic data in a non-disruptive manner.

The present invention further seeks to provide a patient monitoring system comprising such a patient monitor control unit.

The present invention further seeks to provide to computer-implemented method of controlling a patient monitor that causes the patient monitor to display haemodynamic data that can cause the patient monitor to display accurate haemodynamic data in a non-disruptive manner.

The present invention further seeks to provide a computer program product for implementing such a method.

According to an aspect, there is provided a patient monitor control unit comprising a processor arrangement adapted to receive a series of ultrasound measurements received from (acquired by) a sensor comprising at least one configurable ultrasound transducer; process said series of ultrasound measurements to obtain haemodynamic data of a patient coupled to the sensor; control a patient monitor to display the obtained haemodynamic data; evaluate the obtained haemodynamic data to detect a variance in said data; and generate a reconfiguration signal for the at least one configurable ultrasound transducer, wherein the timing of said generation is a function of said evaluation.

The present invention leverages the evaluation of the haemodynamic data derived from the obtained series of ultrasound measurements can be used to decide when the ultrasound sensor needs to be reconfigured or recalibrated to reduce the risk of the haemodynamic data displayed on the patient monitor causing the generation of unnecessary alarms, e.g. when periodically recalibrating the ultrasound sensor. Such recalibration may lead to a change in the signal to noise ratio of the ultrasound measurements, i.e. the acquired ultrasound echoes, which can cause a sudden change in the values of the haemodynamic data, which in turn can cause the generation of an alarm. Such periodic recalibrations should therefore be performed with minimal impact on the visualization of the haemodynamic data.

On the other hand, where a sudden change in the alignment of the ultrasound sensor relative to the artery (or the organ of interest) being monitored causes the haemodynamic data to become unreliable or even unavailable, an immediate recalibration or even repositioning of the ultrasound sensor may be required to restore the desired ultrasound signals. In an embodiment, the processor arrangement therefore is adapted to compare the variance against a defined threshold and to time the generation of the reconfiguration signal as a function of said comparison. In this manner, where the variance remains within physiologically acceptable ranges, i.e. ranges that define normal variances of the haemodynamic data during one or more cardiac cycles of the patient, there is no need for immediate reoptimization of the ultrasound sensor positioning, such that the periodic optimization of the ultrasound sensor can be performed at a point in time where such optimization does not affect the haemodynamic data displayed on the patient monitor.

For example, the patient monitor may have a dedicated display region onto which the haemodynamic data is displayed, the haemodynamic data of a single series of ultrasound measurements spanning the full width of said dedicated display region, and wherein the processor arrangement may be adapted to generate the reconfiguration signal in between successive series of ultrasound measurements if the detected variance is below the defined threshold. Consequently, as the reconfiguration of the ultrasound sensor is performed whilst the patient monitor reinitializes the displaying of the haemodynamic data in order to display the haemodynamic data derived from the next series of ultrasound measurements, no sudden changes in the haemodynamic data resulting from the reconfiguration of the wearable ultrasound sensor are displayed on the patient monitor.

The processor arrangement may be adapted to immediately generate the reconfiguration signal if the detected variance exceeds the defined threshold as in this scenario either the haemodynamic data has become unreliable or the patient needs medical attention, such that by repeating the measurement with a reconfigured sensor a distinction between these two options can be made.

In a further refinement, the processor arrangement is adapted to receive vital signs information of the patient from a further sensor; compare the detected variance against the received vital signs information; and immediately generate the reconfiguration signal in case of the detected variance deviating from the received vital signs information. In such a case the variance is most likely caused by a loss of alignment of the wearable ultrasound sensor relative to the artery being monitored, such that reconfiguration of the wearable ultrasound sensor is required to potentially restore this alignment.

The processor arrangement may be further adapted to change a visualization of the obtained haemodynamic data on the patient monitor in response to detecting said variance in order to warn an observer of the patient monitor that the displayed haemodynamic data may have become unreliable. This may be preferable over the generation of an audible alarm as such as alarm will attract a caregiver to address the needs of the patient, whereas upon reconfiguration of the wearable ultrasound sensor it may prove that such an alarm was false, e.g. where the variance was caused by a loss of alignment of the wearable ultrasound sensor.

The processor arrangement may be further adapted to receive a further series of ultrasound measurements received from the wearable sensor; process said further series of ultrasound measurements to obtain further haemodynamic data of the patient; compare the further haemodynamic data with the haemodynamic data; and generate an alarm if the further haemodynamic data differs from the haemodynamic data by less than a defined amount. In this case, the reconfiguration of the wearable ultrasound sensor did not significantly affect the haemodynamic data, such that it is most likely that in this case the change in the haemodynamic data is caused by a physiological change of the patient, who therefore may require medical attention.

Such an alarm may be an audible alarm generated by the patient monitor or alternatively may be a signal that generate the alarm on a remote electronic device such as a pager, smart phone or the like. To this end, the patient monitor control unit further comprises a communication module for communicating with an external device, and wherein the processor arrangement is further adapted to transmit the generated alarm to the external device with the communication module. In this manner, a caregiver in a remote location (outside audible range of the patient monitor) may still be alerted to the patient requiring medical attention.

According to another aspect, there is provided a patient monitoring system comprising the patient monitor control unit according to any of the herein described embodiments, a patient monitor under control of the patient monitor control unit and a sensor comprising at least one configurable ultrasound transducer communicatively coupled to the patient monitor control unit. Such a patient monitoring system may be used to continuously monitor the haemodynamic data of the patient whilst minimizing the generation of false alarms by the patient monitor as explained above.

In an embodiment, the processor arrangement further is adapted to configure the at least one configurable ultrasound transducer. To this end, the processor arrangement may be adapted to configure the at least one configurable ultrasound transducer by systematic adjustment at least one of: the ultrasound beam angle produced by the sensor (wearable sensor), density of the ultrasound beams within a scanning plane (or a volume), frequency of the ultrasound beam, etc. in order to optimize the signal-to-noise ratio of the echo signals acquired with the wearable ultrasound sensor.

According to yet another aspect, there is provided a computer-implemented method of operating a patient monitor control unit, the method comprising receiving a series of ultrasound measurements received from a sensor comprising at least one configurable ultrasound transducer; processing said series of ultrasound measurements to obtain haemodynamic data of a patient coupled to (or wearing) the sensor (or wearable sensor); controlling a patient monitor to display the obtained haemodynamic data; evaluating the obtained haemodynamic data to detect a variance in said data; and generating a reconfiguration signal for the at least one configurable ultrasound transducer, wherein the timing of said generation is a function of said evaluation. As explained above, such a method ensures that reconfiguration of the sensor is performed whilst minimizing the disruption of the continuity of the haemodynamic data are displayed on the patient monitor by evaluation of this data and implementing a smart reconfiguration strategy that ensures that such disruption is minimized.

For example, in a scenario where the patient monitor has a dedicated display region onto which the haemodynamic data is displayed, the haemodynamic data of a single series of ultrasound measurements spanning the full width of said dedicated display region, the method further may comprise comparing the variance against a defined threshold; and generating the reconfiguration signal in between successive series of ultrasound measurements if the detected variance is below the defined threshold such that any change in the values of the haemodynamic data caused by such reconfiguration are not visualized on the patient monitor.

On the other hand, the method may further comprise immediately generating the reconfiguration signal if the detected variance exceeds the defined threshold as in this case the patient may need immediate medical attention as explained above.

According to still another aspect, there is provided a computer program product comprising a computer readable storage medium having computer readable program instructions embodied therewith for, when executed on the processor arrangement of the patient monitor control unit of any of the herein described embodiments, cause the processor arrangement to implement the method of any of the herein described embodiments. Such a computer program product may be used to configure existing patient monitoring systems to implement the embodiments of the present invention, thereby avoiding the need for such existing patient monitoring systems to be replaced. As such, the availability of such a computer program product is a cost-effective manner of implementing the embodiments of the present invention.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
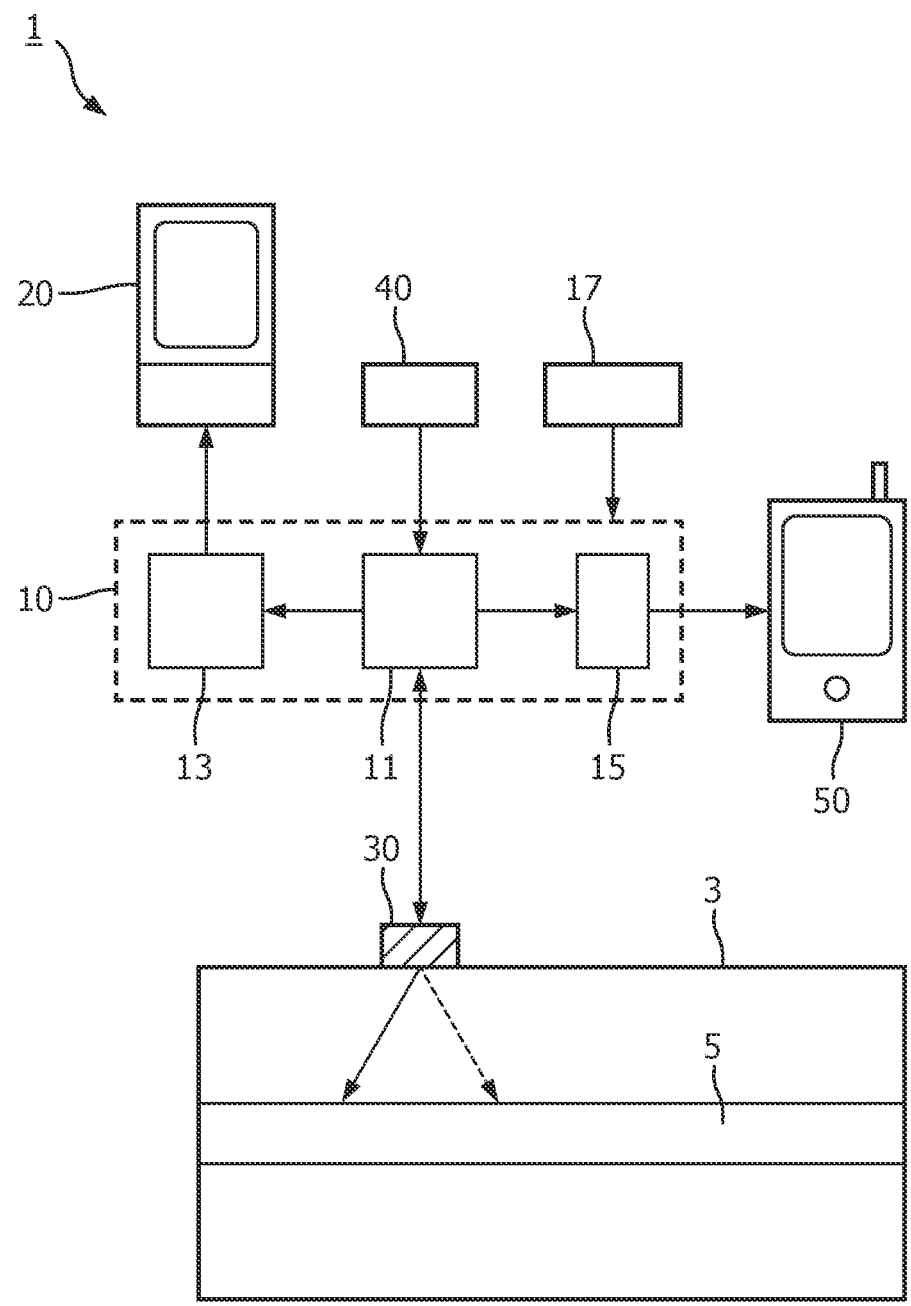
FIG. 1 schematically depicts a patient monitoring system according to an embodiment.

It should be understood that the Figures are merely schematic and are not drawn to scale. It should also be understood that the same reference numerals are used throughout the Figures to indicate the same or similar parts.

FIG. 1 schematically depicts a patient monitoring system 1 according to an example embodiment of the present invention. The patient monitoring system 1 comprises a patient monitor 20 under control of a patient monitor control unit 10. The patient monitor control unit 10 is adapted to receive ultrasound signals, e.g. ultrasound Doppler signals or image data, from an ultrasound sensor 30, which is in case of the wearable embodiment is positioned on a body portion 3 such as an arm or a leg of a patient in order to monitor an artery 5 within the body portion 3. More particularly, the wearable ultrasound sensor 30 typically is arranged to obtain a series of ultrasound measurements from which the patient monitor control unit 10 can derive haemodynamic data pertaining to the blood flow through the artery 5 of the patient and control the patient monitor 20 to display the derived haemodynamic data on the display screen of the patient monitor 20. The ultrasound sensor 30 can be either a wearable ultrasound sensor or a transesophageal echocardiography (TEE) probe coupled to patient (placed into the patient's esophagus) and arranged to acquire ultrasound data representative of the internal structures of the heart and the heart's major vessel.

The patient monitor control unit 10 typically comprises a processor arrangement including one or more processors, here depicted by way of non-limiting example by a computing unit 11 that receives the ultrasound measurement data from the ultrasound sensor 30 and processes the received ultrasound measurement data to obtain the haemodynamic data to be displayed on the patient monitor 20 and optionally to perform evaluations of the obtained haemodynamic data such as to determine trends in the haemodynamic data over time such as a variance in the haemodynamic data across a series of ultrasound measurements received from the wearable ultrasound sensor 30. In the context of the present application, where reference is made to a series of ultrasound measurements it should be understood that this refers to a plurality of measurements performed during one or more cardiac cycles of the patient from which the haemodynamic data pertaining to these cardiac cycles can be derived. The ultrasound measurements comprise at least one of: ultrasound Doppler measurements, measurements performed on ultrasound B mode or M mode data, from which such haemodynamic data can be derived. The processor arrangement as shown in FIG. 1 further comprises a synchronization unit 13 that synchronizes between the computing unit 11 and the patient monitor 20, for example to avoid a reconfiguration of the ultrasound sensor 30 causing a disruption of the continuity of the haemodynamic data displayed on the patient monitor 20. Although the computing unit 11 and the synchronization unit 13 are shown as separate entities, it will be immediately apparent to the skilled person that such units may be realized by a single processor or a plurality of processors working together, e.g. separate processors or discrete processor cores of a single multi-core processor.

The patient monitor control unit 10 may be responsive to the user interface 17, which may take any suitable form. For example, the user interface 17 may be a touchscreen of the patient monitor 20 or of a separate device that is communicatively coupled to the patient monitor control unit 10 in a wired or wireless fashion. Alternatively, the user interface 17 may take the form of a touchpad, keyboard, mouse, trackball and so on or combinations thereof as will be immediately apparent to the skilled person. The user interface 17 may be used by a user of the patient monitoring system 1 to configure which haemodynamic data is to be displayed on the display screen of the patient monitor 20. For example, the user may select one or more haemodynamic waveforms such as (beat-to-beat variability in) flow or peak flow, velocity and vascular diameter (PFV, PVV and VDV) and derived parameters such as arterial perfusion, circulatory volume status, fluid responsiveness and haemodynamic status to be displayed on the patient monitor 20, potentially together with an ultrasound image of the patient's artery as captured by the wearable ultrasound sensor 30.

The patient monitor control unit 10 may be responsive to a further patient monitoring device such as a ventilator, an ECG monitoring device and so on from which the patient monitor control unit 10 receives further vital signs information of the patient being monitored with the wearable ultrasound sensor 30. As will be readily understood by the skilled person, the user of the patient monitoring system 1 may configure the system to also display such further vital signs information onto the patient monitor 20, e.g. through the user interface 17.

The patient monitor control unit 10 may further comprise an alarm generation unit 15 for generating an alarm when the computing unit 11 detects an anomaly in the haemodynamic data derived from the series of ultrasound measurements received from the wearable ultrasound sensor 30. Such an alarm generation unit 15 may take any suitable form such as that of a loudspeaker or the like for generating an audible alarm, a communication module for transmitting the alarm to a remote device 50 such as a pager, smart phone or the like in order to alert a caregiver to the fact that such an anomaly has been detected. Such a communication module may be a wireless communication module implementing any suitable wireless communication standard such as Wi-Fi, Bluetooth, a mobile communication standard such as GSM or UMTS, and so on. Alternatively, the communication module may be a wired communication module that relays the alarm signal to a remote device 50 over a wired network using any suitable communication protocol. The alarm generation unit 15 in yet another embodiment is adapted to generate both an audible alarm as well as alarm signal for the remote device 50.

The wearable ultrasound sensor 30 may comprise a plurality of ultrasound transducers such as piezoelectric transducers or preferably capacitive micro-machined ultrasound transducers (CMUTs), which may be individually addressable in order to configure the operation of the wearable ultrasound sensor 30. For example, the individual addressing of the ultrasound transducers may be controlled to configure the beam angle of the ultrasound beam produced with the wearable ultrasound sensor 30 as indicated by the solid and dashed arrows emanating from the wearable ultrasound sensor 30 in FIG. 1. Such configuration of the wearable ultrasound sensor 30 may be used to bring the artery 5 of the patient in the field of view of the wearable ultrasound sensor 30 after placement of the wearable ultrasound sensor 30 on the body region 3 of the patient. In another example, the reconfiguration signal provided to the configurable ultrasound transducer can be an instruction of varying a frequency of the ultrasound beam. In particular, this embodiment may be realized in an optimized way using the CMUT transducers, because their operational frequency can be varied in a larger frequency range (from about 1 to 8 MHz) compared to the piezoelectric transducers. Scattering of the ultrasound beam by a tissue is revers proportional to the ultrasound beam's frequency, thus if a vessel moves deeper in the tissue, while the sensor is monitoring, a reduction of the frequency of the ultrasound beam would improve the beam's penetration into said tissue. In yet another example, the reconfiguration signal may be an instruction of varying a density of the ultrasound beams within a scanning plane (or a volume). The density and frequency of the ultrasound beam sonicating a region of interest defines a resolution of ultrasound data acquired from this region. However, an increased density, thereby resolution, might require a longer scanning time in order to obtain the ultrasound data of the given region of interest. Therefore, it might be desirable only, when specific evaluation criteria of the obtained haemodynamic data are met, to increase the density of the ultrasound beam. Configurations of the ultrasound transducer presented above help enabling improved signal to noise ratio of the ultrasound measurements (acquired data) thereby improving a quality of the derived therefrom haemodynamic data.

The wearable ultrasound sensor 30 may come in any suitable form, such as an adhesive patch, a sensor that is strapped to the body portion 3 or a combination thereof. Other suitable embodiments of the wearable ultrasound sensor 30 for securing the wearable ultrasound sensor 30 to the body region 3 of the patient will be immediately apparent to the skilled person. The wearable ultrasound sensor 30 may comprise a configuration unit (not shown) responsive to the synchronization unit 13 of the patient monitor control unit 10, which configuration unit may be adapted to configure the wearable ultrasound sensor. Alternatively, the processor arrangement of the patient monitor control unit 10, e.g. the computing unit 11 and/or the synchronization unit 13 may be adapted to configure the wearable ultrasound sensor 30 as will be explained in more detail below.

Figure 2:
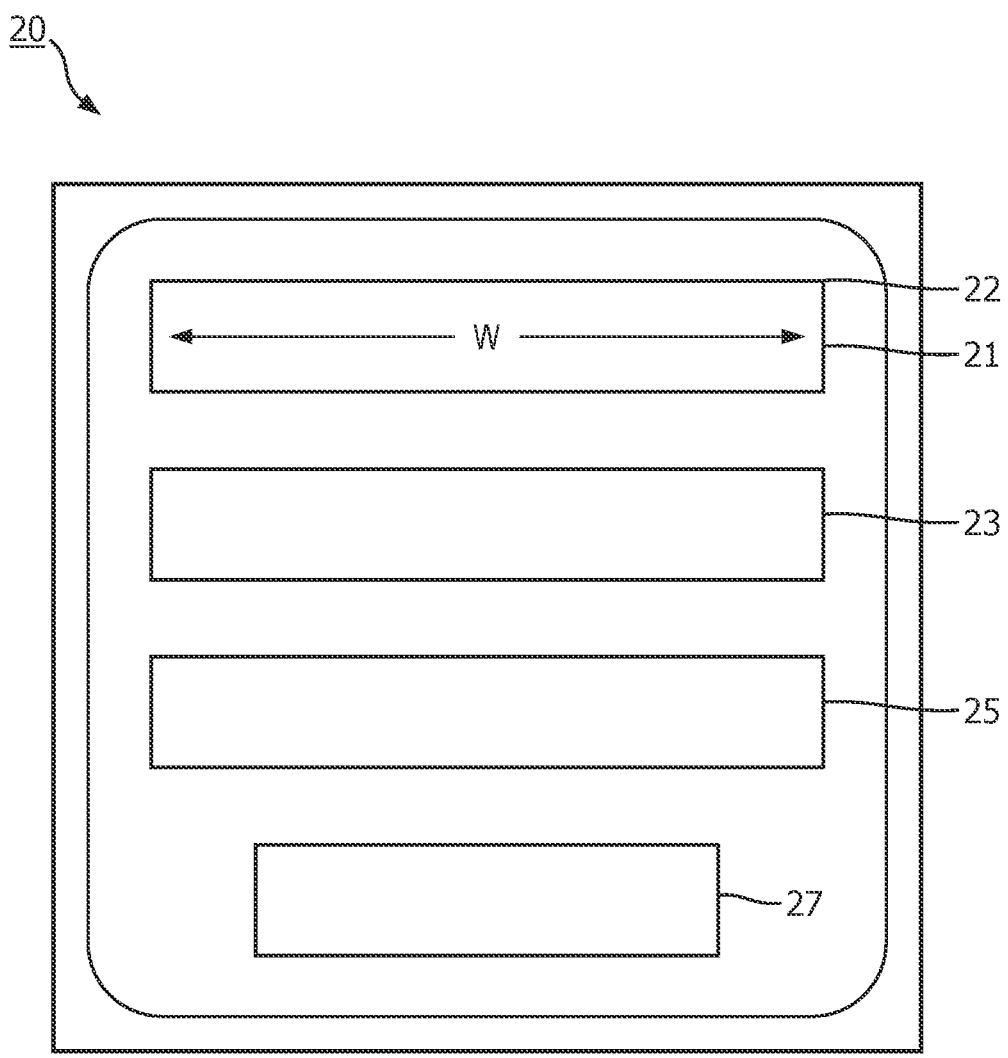
FIG. 2 schematically depicts the display screen of a patient monitor according to an example embodiment.

FIG. 2 schematically depicts an example configuration of the display screen of the patient monitor 20 on which a number of display regions 21, 23, 25 and 27 are shown. Such display regions may be used to display different types of relevant information, such as patient ID, wearable ultrasound sensor ID, continuous graphs of the monitored haemodynamic data or parameters derived therefrom as previously explained, trends in the monitored haemodynamic data or parameters derived therefrom and ultrasound images captured with the wearable ultrasound sensor 30. Where a display region 21 is dedicated to the display of the monitored haemodynamic data, e.g. graphs or trends of such data or its derived parameters, the data is typically displayed as a trace that progresses from left to right across the display screen until the trace reaches the end point 22 of the display region 21. At this point in time, the display region is refreshed and a new trace is shown beginning at the opposite end of the display region 21 as is well-known per se. The display region 21 may have a width W such that a trace spanning the width W of the display region 21 covers the haemodynamic data or parameters derived thereof of exactly one series of ultrasound measurements captured with the wearable ultrasound sensor 30. Such a series may include any suitable number of cardiac cycles of the patient as previously explained. Typically, such a series will include a plurality of cardiac cycles.

One of the key insights of the present invention at least in some embodiments is that when the display screen of the patient monitor 20 is refreshed following the trace of the haemodynamic data or parameters derived thereof of a complete series of ultrasound measurements reaching the end point 22 of the dedicated display region 21 displaying this trace, a change in the magnitude of this data or derived parameters will be difficult to notice because the next data point, i.e. the first data point derived from the next series of ultrasound measurements, is shown at the opposite end of the dedicated display region 21. Such a change in magnitude for example may be expected when the wearable ultrasound sensor 30 is reconfigured, e.g. its beam properties (angle, density, frequency, etc.) is readjusted, as this typically causes a change in the intensity of the Doppler signals obtained with the wearable ultrasound sensor 30. Such periodic reconfiguration of the wearable ultrasound sensor 30 may be desirable in order to ensure that the haemodynamic data derived from the ultrasound measurements (acquired ultrasound data) performed with the wearable ultrasound sensor 30 remain reliable over a prolonged period of time, e.g. to counteract small changes in the alignment of the wearable ultrasound sensor 30 relative to the artery 5 of the patient.

Therefore, in at least some embodiments of the present invention, the processor arrangement of the patient monitor control unit 10 is adapted to generate a reconfiguration signal at the end of a complete series of ultrasound measurements, i.e. in between successive series of ultrasound measurements such that any associated change in the magnitude of the haemodynamic data or parameters derived therefrom is not apparent on the patient monitor 20 due to the fact that this change in magnitude does not appear within a trace displayed in the dedicated display region 21 of the patient monitor 20 but instead appears in between traces during the refreshing of the patient monitor 20. Such periodic reconfiguration of the wearable ultrasound sensor 30 may occur at any suitable frequency, e.g. after each complete series of ultrasound measurements or after the completion of N series of ultrasound measurements in which N is a positive integer having a value of at least 2.

Figure 3:
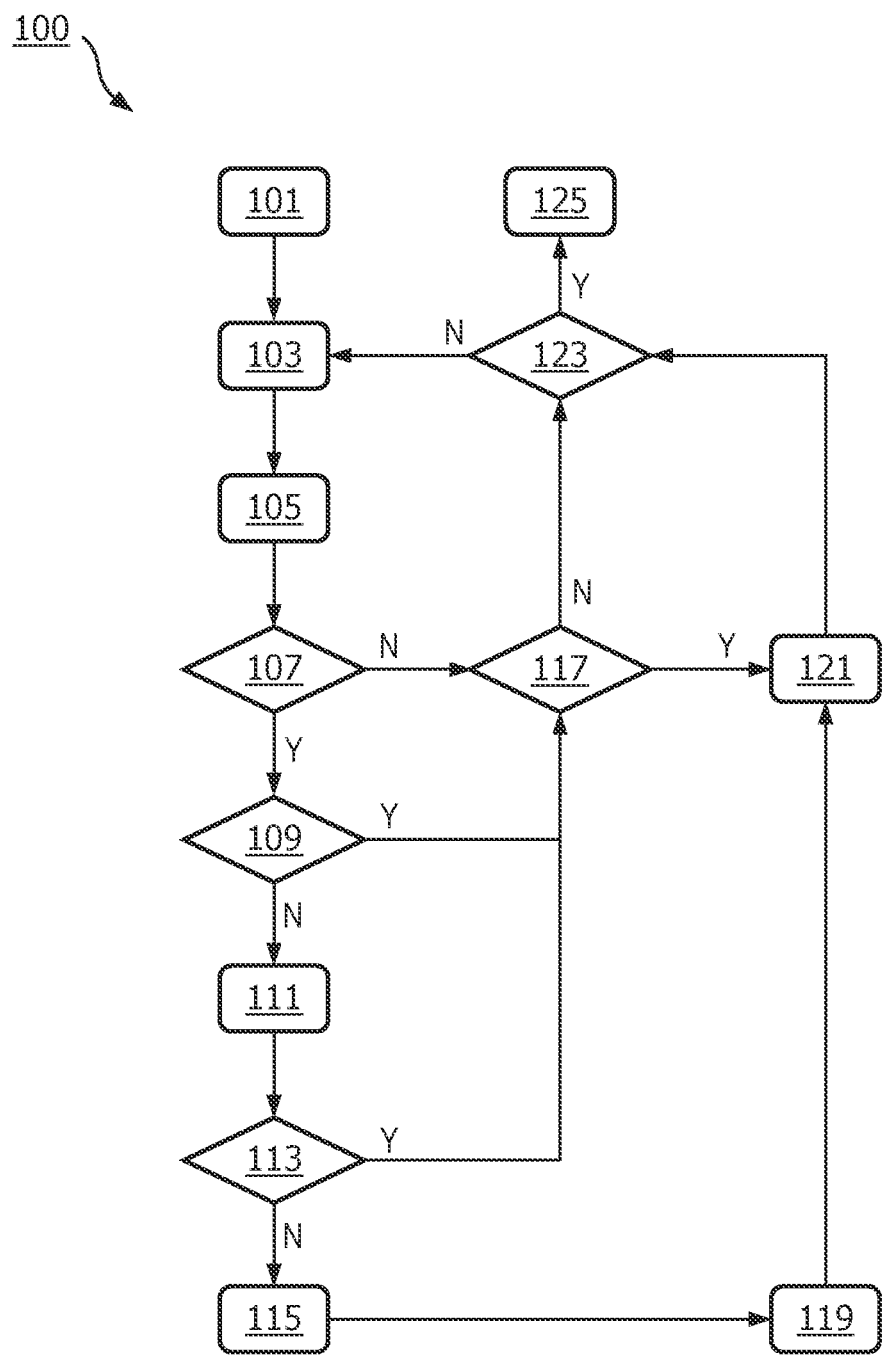
FIG. 3 is a flowchart of an example method implemented on a patient monitoring system according to an embodiment.

This reconfiguration strategy may be deployed where the computing unit 11 considers that the haemodynamic data derived from the ultrasound measurements is stable enough to warrant the delay of the reconfiguration of the wearable ultrasound sensor 30 to the end of a trace displayed in the dedicated display region 21 of the patient monitor 20, i.e. at the completion of a series of ultrasound measurements performed with the wearable ultrasound sensor 30. However, if the computing unit 11 considers that the haemodynamic data derived from the ultrasound measurements is likely to have become unstable or unreliable, an immediate reconfiguration of the wearable ultrasound sensor 30 may be forced by the generation of a reconfiguration signal with the synchronization unit 13 and the provision of the signal to the wearable ultrasound sensor 30. Such an immediate reconfiguration of the wearable ultrasound sensor 30 therefore may take place during a series of ultrasound measurements such that the trace displayed in the dedicated display region 21 of the patient monitor 20 may exhibit a sudden change in the magnitude of the displayed haemodynamic data or parameters derived thereof as caused by the reconfiguration of the wearable ultrasound sensor 30. This will be explained in further detail with the aid of FIG. 3, which depicts a flowchart of a method 100 implemented by the processor arrangement of the patient monitor control unit 10.

The method 100 commences in operation 101 with the (manual) positioning of the wearable ultrasound sensor 30 on the body region 3 of the patient and the initial configuration of the wearable ultrasound sensor 30 in order to bring the artery 5 within the body region 3 of the patient into the field of view of the wearable ultrasound sensor 30. This will be explained in further detail with the aid of FIG. 4 and FIG. 5, which will be described below. Upon the initial configuration of the wearable ultrasound sensor 30 in this manner, the method 100 proceeds to operation 103 in which the patient monitor control unit 10 receives the ultrasound measurements (acquired ultrasound data) from the wearable ultrasound sensor 30 and processes those measurements as explained above in order to derive the haemodynamic data and associated parameters from the received ultrasound measurements, and displays the derived data and associated parameters of the patient monitor 20 in accordance with a user-specified configuration of the patient monitor 20 for instance as previously explained.

In operation 105, the computing unit 11 of the patient monitor control unit 10 evaluates the haemodynamic data (or the parameters derived therefrom) to detect a beat-to-beat variance in the haemodynamic data derived from the ultrasound measurements. For example, the computing unit 11 may compare successive data points relating to the same phase of the cardiac cycle but belonging to different heartbeats in order to detect such a variance. The computing unit 11 then proceeds to operation 107 in which the variance between such data points (including a zero variance) is compared against a defined threshold. This threshold typically represents a physiologically relevant threshold. In other words, a variance below this threshold is unlikely to represent a physiologically relevant event, whereas a variance above this threshold is likely to represent a physiologically relevant event, that is, a physiological change in the patient being monitored, which may be indicative of the patient requiring urgent medical attention.

If the detected variance is below this defined threshold, the method proceeds to operation 117 in which it is checked if the trace displayed in the dedicated region 21 of the patient monitor 20 has reached the endpoint 22 of the dedicated region 21. If this is the case, the method 100 proceeds to operation 121 in which the synchronization unit 13 generates the reconfiguration signal for the wearable ultrasound sensor 30 in order to reconfigure the wearable ultrasound sensor 30 whilst the patient monitor 20 is refreshing as previously explained, after which the method 100 proceeds to operation 123 in which it is checked if the monitoring of the patient is to be continued. If this is the case, the method 100 returns to previously described operation 103, whereas if the monitoring of the patient is to be terminated the method 100 terminates in operation 125. Similarly, if it is decided in operation 117 that the trace displayed in the dedicated region 21 of the patient monitor 20 has not yet reached the endpoint 22, the method proceeds to the previously described operation 123 or alternatively returns directly to operation 103 (not shown).

If the evaluation of the detected variance in operation 107 determines that this variance is above the defined threshold, the method 100 proceeds to operation 109 in which the detected variance in the haemodynamic data derived from the ultrasound measurements provided by the wearable ultrasound sensor 30 is compared against vital signs data provided by the further device(s) 40. If the vital signs data provided by the further device(s) 40 shows a similar variance, then the variance detected in the haemodynamic data is indicative of an actual physiological change in the patient such that the alarm generation unit 15 of the patient monitor control unit 10 may generate the aforementioned alarm to attract the attention of a caregiver such that the patient can receive the necessary medical attention. In this scenario, no immediate reconfiguration of the wearable ultrasound sensor 30 is required such that the method 100 proceeds to the previously described operation 117.

Alternatively, the alarm generation unit 15 may be adapted to immediately generate the alarm upon detecting a variance in the haemodynamic data above the defined threshold, with the alarm being terminated if the comparison of the variance in the haemodynamic data with the vital signs data provided by the further device(s) 40 shows that the variance in the haemodynamic data is unexpected, i.e. is not replicated in the vital signs data as in such a scenario the variance is unlikely to be the result of an actual physiological change in the patient but instead is likely to be caused by a change in the alignment of the wearable ultrasound device 30 relative to the artery 5 of the patient.

In such a case, the method 100 may proceed to operation 111 in which the visualization of the haemodynamic data on the patient monitor is altered to indicate that the displayed haemodynamic data values (or parameter values) have become unreliable. This for example may be achieved by changing the color of the trace displayed in the dedicated display region 21 and/or by changing the color of a numerical value displayed on the patient monitor 20. Additionally or alternatively, the computing unit 11 may calculate a reliability score for the haemodynamic data to be displayed on the patient monitor 20 and control the patient monitor 20 to display this reliability score such that a change, e.g. a reduction, of this score is indicative of the haemodynamic data potentially having become unreliable.

The method 100 subsequently proceeds to operation 113 in which a reconfiguration signal for the wearable ultrasound sensor 30 is immediately generated with the synchronization unit 13 in order to perform an electronic recalibration of the wearable ultrasound sensor 30 in order to realign the wearable ultrasound sensor 30 with the artery 5 of the patient. Upon performing this recalibration, a further series of ultrasound measurements is received from the wearable ultrasound sensor 30 from which further haemodynamic data is extracted and compared against the haemodynamic data obtained prior to the recalibration of the wearable ultrasound sensor 30. If the further haemodynamic data is sufficiently different to the pre-recalibration haemodynamic data, i.e. the variance between a data point in the further haemodynamic data and a data point in the pre-recalibration haemodynamic data prior to the misalignment of the wearable ultrasound sensor 30 is below the defined threshold, the electronic recalibration of the wearable ultrasound sensor 30 has been successful such that the method 100 may proceed to the previously described operation 117.

On the other hand, if the further haemodynamic data is substantially similar to the pre-recalibration haemodynamic data, i.e. the variance between a data point in the further haemodynamic data and a data point in the pre-recalibration haemodynamic data prior to the misalignment of the wearable ultrasound sensor 30 remains above the defined threshold, the electronic recalibration of the wearable ultrasound sensor 30 has been unsuccessful, in which case the method 100 proceeds to operation 115 in which the alarm generating unit 15 of the patient monitor control unit 10 generates an alarm for the caregiver to manually reposition the wearable ultrasound sensor 30 in operation 119, after which the method 100 proceeds to operation 121 in which the electronic recalibration of the wearable ultrasound sensor 30 is performed as previously explained. It is noted for the avoidance of doubt that operation 119 is not performed by the processor arrangement of the patient monitor control unit 10 and as such does not form part of any of the computer-implemented methods that are claimed as part of the present application.

Figure 4:
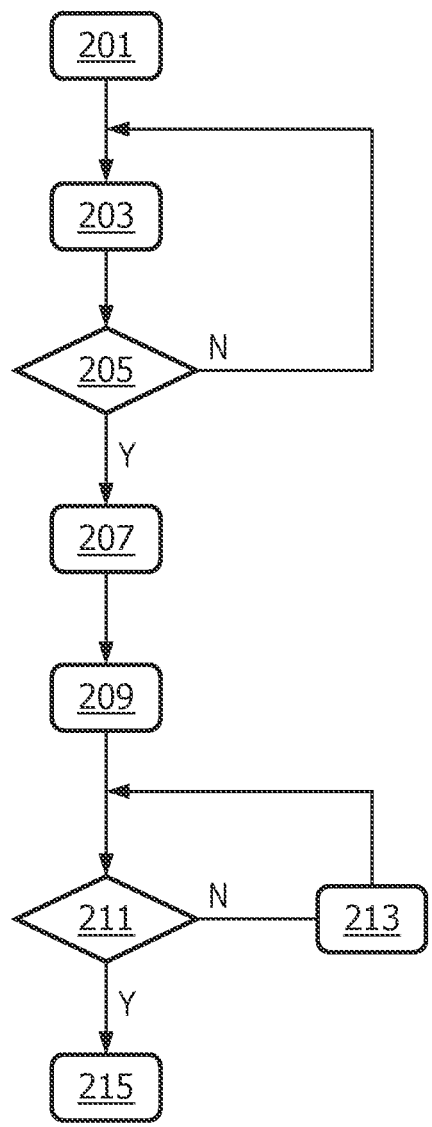
FIG. 4 is a flowchart of a configuration method for a 2-D ultrasound patch.

At this point, the positioning and calibration of the wearable ultrasound sensor 30 will be explained in further detail with the aid of FIG. 4, which depicts a flowchart of a positioning and calibration method of the wearable ultrasound sensor 30, here a 2-D ultrasound sensor. The method commences in operation 201 with the provision of the wearable ultrasound sensor 30 after which the method proceeds to operation 203 in which the wearable ultrasound sensor 30 is manually positioned onto the body region of the patient by the caregiver and the wearable ultrasound sensor 30 is electronically calibrated, e.g. by systematic variation of the beam angle generated by the wearable ultrasound sensor 30 in order to detect an artery 5 of the patient in the Doppler ultrasound data generated with (acquired by) the wearable ultrasound sensor 30. It is checked in operation 205 if such an artery 5 can be detected. If such an artery 5 cannot be detected, the method returns to operation 203 in which the caregiver manually repositions the wearable ultrasound sensor 30 after which its electronic calibration is repeated until the artery 5 is found after which the method proceeds to operation 207.

In operation 207, a region of interest close to the artery 5 is selected and in operation 209 a biplane view of the artery is generated to check alignment of the wearable ultrasound sensor 30 with the artery 5 in operation 211. In operation 211, the respective diameters of the artery 5 are evaluated systematically by manual repositioning of the wearable ultrasound sensor 30 by the caregiver in operation 213, optionally aided by acoustic guidance signals generated by the alarm generating unit 15 until the maximum diameter of the artery 5 in both view planes is obtained, which is indicative of the optimal alignment of the wearable ultrasound sensor 30 with the artery 5. Upon achieving such an optimal alignment, the method terminates in operation 215.

Figure 5:
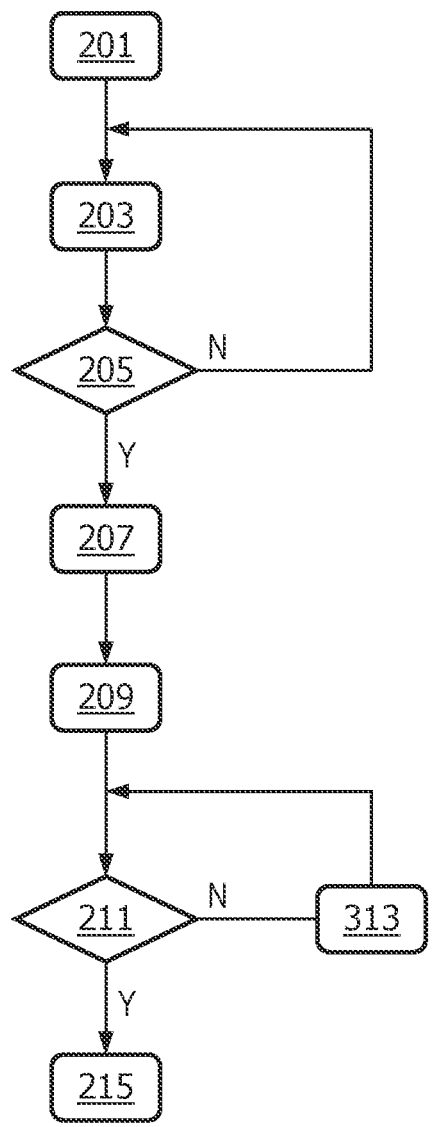
FIG. 5 is a flowchart of a configuration method for a 3-D ultrasound patch.

FIG. 5 depicts a flowchart of a positioning and calibration method of the wearable ultrasound sensor 30, here a 3-D ultrasound sensor. The method in FIG. 5 differs from the method as shown in FIG. 4 for a 2-D wearable ultrasound sensor 30 in that the manual repositioning of the wearable ultrasound sensor 30 in operation 213 to optimize the alignment of the wearable ultrasound sensor 30 with the artery 5 of the patient is replaced by operation 313 in which this repositioning is performed by electronic beam steering of the wearable 3-D ultrasound sensor 30.

The above described embodiments of the method 100 executed by the processor arrangement of the patient monitor control unit 10 may be realized by computer readable program instructions embodied on a computer readable storage medium having, when executed on the processor arrangement, cause the processor arrangement to implement any embodiment of the method 100. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the patient monitor control unit 10 is adapted to retrieve the computer readable program instructions from such a computer readable storage medium and to create a new computer readable storage medium by storing the retrieved computer readable program instructions in a data storage arrangement of the patient monitor control unit 10, e.g. in a memory device or the like forming part of the patient monitor control unit 10.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A patient monitoring processor configured to:
   receive a series of ultrasound measurements received from a sensor, said sensor comprising at least one configurable ultrasound transducer;
   process said series of ultrasound measurements to obtain hemodynamic data of a patient coupled to the sensor;
   control a patient monitor to display the obtained hemodynamic data;
   evaluate the obtained hemodynamic data to detect a variance in said data, the variance comprising a difference between successive data points relating to a same phase of a cardiac cycle and belonging to different heartbeats;
   receive vital signs information of the patient from a further sensor;
   compare the detected variance against the received vital signs information; and
   immediately generate a reconfiguration signal in case of the detected variance deviating from the received vital signs information.

2. The patient monitoring processor of claim 1, wherein the processor is further configured to compare the variance against a defined threshold and to time the generation of the reconfiguration signal as a function of said comparison.

3. The patient monitoring processor of claim 2, further comprising:
   the patient monitor under control of the patient monitoring processor, wherein the patient monitor has a dedicated display region onto which the hemodynamic data is displayed, the hemodynamic data of a single series of ultrasound measurements spanning a full width of said dedicated display region, and wherein the processor is further configured to generate the reconfiguration signal in between successive series of ultrasound measurements if the detected variance is below the defined threshold.

4. The patient monitoring processor of claim 3, wherein the processor is further configured to change a visualization of the obtained hemodynamic data on the patient monitor in response to detecting said variance.

5. The patient monitoring processor of claim 3, wherein the processor is further configured to:
   receive a further series of ultrasound measurements received from the sensor;
   process said further series of ultrasound measurements to obtain further hemodynamic data of the patient;
   compare the further hemodynamic data with the hemodynamic data; and
   generate an alarm if the further hemodynamic data differs from the hemodynamic data by less than a defined amount.

6. The patient monitoring processor of claim 5, further comprising a communication module for communicating with an external device, and wherein the processor is further configured to transmit the generated alarm to the external device with the communication module.

7. The patient monitoring processor of claim 1, wherein the processor is further configured to configure the at least one configurable ultrasound transducer by systematic adjustment of at least one of a density of the ultrasound beams produced by the sensor and a frequency of the ultrasound beams.

8. A patient monitoring system, comprising:
   a patient monitoring processor configured to:
   receive a series of ultrasound measurements received from a sensor, said sensor comprising at least one configurable ultrasound transducer;
   process said series of ultrasound measurements to obtain hemodynamic data of a patient coupled to the sensor;
   control a patient monitor to display the obtained hemodynamic data;
   evaluate the obtained hemodynamic data to detect a variance in said data, the variance comprising a difference between successive data points relating to a same phase of a cardiac cycle and belonging to different heartbeats;
   receive vital signs information of the patient from a further sensor;
   compare the detected variance against the received vital signs information; and
   immediately generate a reconfiguration signal in case of the detected variance deviating from the received vital signs information;
   a patient monitor under control of the patient monitor processor; and
   the sensor comprising the at least one configurable ultrasound transducer, wherein the sensor is communicatively coupled to the patient monitoring processor.

9. The patient monitoring system of claim 8, wherein the processor is further configured to configure the at least one configurable ultrasound transducer.

10. The patient monitoring system of claim 9, wherein the processor is further configured to configure the at least one configurable ultrasound transducer by systematic adjustment of the ultrasound beam angle produced by the sensor.

11. The patient monitoring system of claim 8, wherein the sensor is either a wearable sensor or a transesophageal echocardiography (TEE) probe.

12. The patient monitoring system of claim 8, wherein the processor is further configured to configure the at least one configurable ultrasound transducer by systematic adjustment of at least one of a density of the ultrasound beams produced by the sensor and a frequency of the ultrasound beams.

13. A computer-implemented method of operating a patient monitoring processor, the method comprising:
   receiving a series of ultrasound measurements received from a sensor comprising at least one configurable ultrasound transducer;
   processing said series of ultrasound measurements to obtain hemodynamic data of a patient coupled to the sensor;
   controlling a patient monitor to display the obtained hemodynamic data;
   evaluating the obtained hemodynamic data to detect a variance in said data, the variance comprising a difference between successive data points relating to a same phase of a cardiac cycle and belonging to different heartbeats;
   receiving vital signs information of the patient from a further sensor;

comparing the detected variance against the received vital signs information; and immediately generating a reconfiguration signal in case of the detected variance deviating from the received vital signs information.

14. The computer-implemented method of claim 13, wherein the patient monitor has a dedicated display region onto which the hemodynamic data is displayed, the hemodynamic data of a single series of ultrasound measurements spanning a full width of said dedicated display region, and wherein the method further comprises:

comparing the variance against a defined threshold; and generating the reconfiguration signal in between successive series of ultrasound measurements if the detected variance is below the defined threshold.

15. The computer-implemented method of claim 14, further comprising immediately generating the reconfiguration signal if the detected variance exceeds the defined threshold.

16. The computer-implemented method of claim 13, further comprising configuring the at least one configurable ultrasound transducer by systematic adjustment of at least one of a density of the ultrasound beams produced by the sensor and a frequency of the ultrasound beams.

17. A non-transitory computer readable medium having computer readable program instructions embodied thereon that, when executed on a processor, cause the processor to:

receive a series of ultrasound measurements from a sensor comprising at least one configurable ultrasound transducer;

process said series of ultrasound measurements to obtain hemodynamic data of a patient coupled to the sensor;

control a patient monitor to display the obtained hemodynamic data;

evaluate the obtained hemodynamic data to detect a variance in said data, the variance comprising a difference between successive data points relating to a same phase of a cardiac cycle and belonging to different heartbeats;

receive vital signs information of the patient from a further sensor;

compare the detected variance against the received vital signs information; and immediately generate a reconfiguration signal in case of the detected variance deviating from the received vital signs information.

* * * * *